US008294104B2

(12) United States Patent
Dos Santos et al.

(10) Patent No.: US 8,294,104 B2
(45) Date of Patent: Oct. 23, 2012

(54) SYSTEM FOR DETECTING AND LOCATING WATER IN A SANDWICH-TYPE STRUCTURE FOR AIRCRAFTS

(75) Inventors: Fernando Manuel Ferreira Dos Santos, Toulouse (FR); Jean-Louis Arnaud, Toulouse (FR)

(73) Assignee: Airbus Operations SAS, Toulouse (FR)

( * ) Notice: Subject to any disclaimer, the term of this patent is extended or adjusted under 35 U.S.C. 154(b) by 611 days.

(21) Appl. No.: 12/093,212

(22) PCT Filed: Nov. 9, 2006

(86) PCT No.: PCT/FR2006/051158
§ 371 (c)(1),
(2), (4) Date: Sep. 24, 2009

(87) PCT Pub. No.: WO2007/057599
PCT Pub. Date: May 24, 2007

(65) Prior Publication Data
US 2010/0155603 A1    Jun. 24, 2010

(30) Foreign Application Priority Data
Nov. 10, 2005 (FR) .................. 05 53415

(51) Int. Cl.
*G01J 5/02* (2006.01)
*G01J 5/00* (2006.01)

(52) U.S. Cl. ................ 250/341.6; 250/338.1

(58) Field of Classification Search ............ 250/341.6, 250/338.1, 341.8; 356/457
See application file for complete search history.

(56) References Cited

U.S. PATENT DOCUMENTS

| | | | |
|---|---|---|---|
| 5,433,106 A | 7/1995 | Matsumura et al. | |
| 7,456,973 B2 | 11/2008 | Steinbichler et al. | |
| 2002/0018510 A1* | 2/2002 | Murphy et al. ............. | 374/45 |
| 2005/0207468 A1* | 9/2005 | McCullough et al. ....... | 374/5 |
| 2007/0090294 A1* | 4/2007 | Safai et al. ............... | 250/341.8 |

FOREIGN PATENT DOCUMENTS

| | | |
|---|---|---|
| CN | 1542426 A | 11/2004 |
| EP | 1455180 A1 * | 9/2004 |
| JP | 61004903 A | 1/1986 |
| JP | 6027061 A | 2/1994 |
| JP | 2000292388 A | 10/2000 |
| JP | 2004335361 A | 11/2004 |

* cited by examiner

*Primary Examiner* — David Porta
*Assistant Examiner* — Faye Boosalis
(74) *Attorney, Agent, or Firm* — Perman & Green, LLP

(57) ABSTRACT

A system for detecting and locating water in a sandwich-type structure for aircrafts, the system including means for heating the water contained in an intermediate layer of the sandwich-type structure, and means for recording at least one image of a surface of the sandwich-type structure, the image showing particular regions of the surface, corresponding to the presence of water in the intermediate layer. The means for heating the water include a device for emitting microwaves inside the sandwich-type structure, at a frequency essentially equal to the resonance frequency of the water molecules. The invention also relates to a method implemented by the system.

9 Claims, 2 Drawing Sheets

SYSTEM FOR DETECTING AND LOCATING WATER IN A SANDWICH-TYPE STRUCTURE FOR AIRCRAFTS

FIELD

The disclosed embodiments pertain to a system for detecting and locating the presence of water in aircraft box structures and, especially, sandwich-type composite structures. The invention can be applied in aeronautics and especially in the maintenance of aircraft structures using non-destructive controls. The invention can be applied more particularly in structures known as box structures, i.e. closed structures made out of composite materials with an external carbon envelope and an internal honeycomb structure.

BRIEF DESCRIPTION OF RELATED DEVELOPMENT

In aeronautics and especially in the maintenance of aircraft in service it is important to detect the presence of water in aircraft structures. Water may be present in certain parts of the aircraft, especially parts made out of sandwich-type composite materials. A sandwich-type material comprises an alveolar or cellular structure forming an internal layer. This internal layer is lined on each side with a skin. The cellular structure may be a honeycomb layer made out of cardboard, such as Nomex® or a honeycomb structure made out of fiberglass or foam. The skins may be made out of an impermeable material. They may be made so as to meet on the edge of the part thus forming an envelope around the cellular structure. The parts thus formed are called box structures. For example landing-gear doors, control surfaces, radomes or again elevators are parts that are often made out of sandwich composite materials.

Now, the presence of water in these parts, especially in the internal layer which is the intermediate layer of the box structure, affects the worthiness and the weight of the structures, and this may cause undesirable performance by the aircraft in flight.

At present, the presence of water in these structures is detected either by regular inspections during the maintenance phase or by signs of its presence (swelling of the structures, condensation spots etc) or again in the most extreme cases, by the effects on mechanical actuators owing to the increase in the weight of the structure.

At present, in an inspection during an aircraft maintenance job, the presence of water in sandwich structures is generally detected by means of an external heat source. In this classic detection technique, the water present within the sandwich structure is heated by means of an external heat source. This heat source may be an oven or a heating pad, i.e. a cover through which there runs a resistor used to heat the entire surface lined with this pad. The heating of the water prompts either a deformation of the structure or an increase in the temperature of the surface of the structure. During the aircraft maintenance phase, if a deformation of the structure or a rise in the temperature of the surface of the structure is detected, the maintenance staff deduces the presence of water in said structure through either an interferometer (shearography system) or an infrared-sensitive camera.

A deformation of the sandwich structure is detected through a method of holographic interferometry. Holographic interferometry is a method of location based on the use of two superimposed holographic images or pictures which reveal the parts of an element in which stresses appear. In other words, holographic interferometry consists of the taking of two holographic images, i.e. two images in relief that are superimposed to reveal the differences between the two pictures. These differences correspond to the deformation of the sandwich structure. It is deduced therefrom that, at the location of the deformation, there is water in the intermediate layer of the sandwich structure.

The increase in the temperature of the surface of the structure is detected by means of a thermal camera or an infrared camera whose particular feature is that, in an image, it reveals areas of the surface of the structure in which the temperature is different. At the position of these areas, there is water in the intermediate layer of the sandwich structure.

However, this technique requires that the structure to be inspected be to heated in order to heat any water that might have infiltrated into the intermediate layer of said structure. Now, it must be noted that certain defects in the construction of the structure, such as for example excess resin or adhesive, show the same heat signature as a honeycomb cell in which water is located. Thus, under the effect of heat, these defects have the same visual representation in images acquired by the camera as water infiltrations. This technique therefore cannot be used to discriminate between defects. The presence of excess resin or adhesive is detected as the presence of water in a cell. The maintenance staff then carries out repairs that are unnecessary.

Furthermore, the fact of heating the entire structure to be inspected entails the use of a device that is relatively bulky and difficult to use: in the case of heating by an oven, the part to be inspected has to be isolated in an oven; in the case of a heating pad, the heating pad has to be installed so as to be properly flat against the part to be inspected and it has to be connected to an electrical power source.

Furthermore, to carry out the inspection of sandwich structures, the aircraft has to be immobilized prior to any repairs in order to find out if there has been any infiltration of water into the structure. The time needed to inspect the aircraft is relatively lengthy, about eight hours. Now, immobilizing an aircraft is costly. In addition to this time of immobilization for inspection, there is the time needed to prepare the structure, about 32 hours, as well as the time needed to disassemble, reassemble and fit the parts that cannot be inspected while in the aircraft. The total time of immobilization of the aircraft is therefore relatively great, and this entails major costs.

SUMMARY

The disclosed embodiments are aimed precisely at overcoming the drawbacks of the techniques set forth here above. To this end, the disclosed embodiments propose a system for heating only the water that has infiltrated into the structure. The outer skin of the sandwich structure is not totally heated. The effect of this is that construction defects in the structure, if any, do not get heated and are therefore not detected by the camera. To this end, the invention proposes to heat the water present in a sandwich structure by means of electromagnetic microwaves generated in the structure to be inspected, these microwaves having the effect of heating the water. The water is then detected by means of a thermal camera or a holographic interferometry device.

This system has the advantage of enabling the easy detection of the presence of water in the structure without requiring any lengthy immobilizing of the aircraft. This means that repairs can be made early and at lower cost.

More specifically, the disclosed embodiments relate to a system for the detection and locating of water in a sandwich structure for aircraft, comprising a means to heat the water present in the intermediate layer of the sandwich structure and means to take at least one image of a surface of the sandwich structure, said image showing noteworthy regions of said surface corresponding to the presence of water in the intermediate layer, characterized in that the means used to heat the water comprise a device (2, 3, 6) for emitting microwaves inside the sandwich structure at a frequency essentially equal to the resonance frequency of the water molecules.

The disclosed embodiments may also comprise one or more of the following characteristics:

the microwave emitter device comprises a microwave generator external to the sandwich structure, at least one microwave emitter situated inside the structure and at least one waveguide to transmit the microwaves from the generator to the emitter.

the microwave generator emits waves at a frequency essentially equal to the resonance frequency of the water molecules.

the means for taking images is an infrared camera or a thermal camera capable of detecting a hot region on the surface of the structure, this hot region corresponding to the presence of water heated by the microwaves.

the means used to take the pictures are a holographic interferometry device capable of detecting the deformed regions on the surface of the sandwich structure, these deformed regions corresponding to the presence of water heated by the microwaves.

the microwave emitting device comprises two microwave emitters.

the two microwave emitters emit at different frequencies.

a microwave emitter is an irremovable antenna.

an irremovable antenna comprises a base fixed to the structure and a conductive rod situated within the structure.

a microwave emitter is a removable antenna.

a removable antenna comprises a conductive rod installed in a hole of the structure, this hole being shut by a tight-sealing plug during flight.

The disclosed embodiments also relate to a method for the detection of water in a sandwich structure for aircraft, characterized by the fact that it comprises the following operations:

emitting microwaves within the sandwich structure, taking at least one image of a surface of the sandwich structure, and detecting a noteworthy region on the image of the surface of said structure, this region corresponding to the presence of water in an intermediate layer of said sandwich structure.

DETAILED DESCRIPTION OF THE EMBODIMENTS

Figure 1:
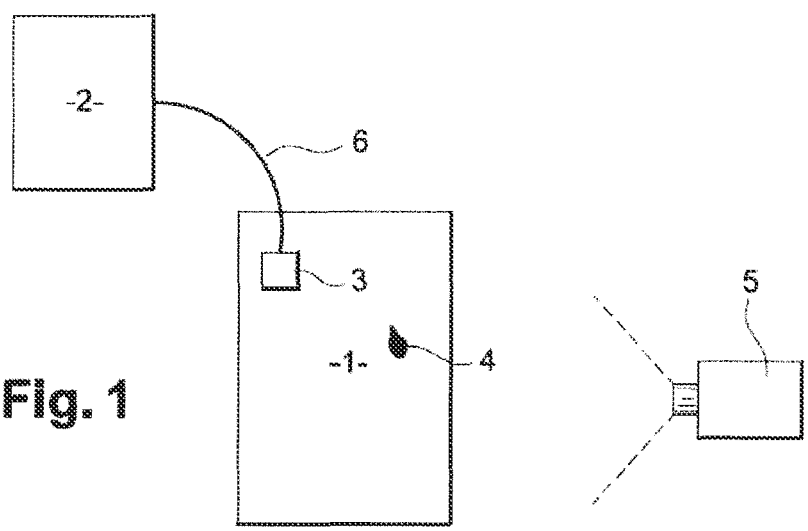
FIG. 1 is a schematic view of an example of a water detection system according to the disclosed embodiments.

The disclosed embodiments relate to a system for detecting the presence of water in a sandwich structure by the injection of microwaves into said structure. A system of this kind is shown schematically in FIG. 1. This FIG. 1 shows an example of a structure to be inspected equipped with the system of the invention. The structure 1 to be inspected is a closed structure or part comprising one or more cells. In the example of FIG. 1, the structure 1 to be inspected is rectangular. It is clear that it can have a variety of shapes, and especially shapes suited to the structure of an aircraft. This structure to be inspected, may, for example, be the front landing-gear door of an aircraft.

The structure to be inspected is a sandwich structure having carbon skins and an intermediate honeycomb layer. The honeycomb structure has the advantage of not absorbing the electromagnetic waves. Carbon has the advantage of being impervious to electromagnetic waves. Thus, with a structure of this kind, the waves injected into the sandwich structure spread through the honeycomb layer between the two carbon skins. When these waves encounter water, they have the effect of heating this water.

As can been seen in FIG. 1, the system of the invention has a device to emit microwaves inside the structure to be inspected. This emitter device comprises a wave generator 2 situated outside the structure to be inspected 1. The waves produced by the generator 2 are microwaves. This emitter device also has an emitter 3 or antenna installed in the structure 1. At least one emitter is mounted in each part of the aircraft to be inspected. The emitter 3 of the part 1 to be inspected is connected to the generator 2 by means of a waveguide 6. This waveguide may be a coaxial cable.

The waveguide 6 sends the emitter 3 microwaves generated by the generator 2. The emitter 3 transmits these microwaves in the internal layer, i.e. the honeycomb layer, of the structure 1. In spreading through the internal layer, the microwaves heat the water present in the structure 1.

In a preferred embodiment, the microwaves are generated at a frequency essentially equal to the resonance frequency of the water molecules. This excites the water molecules. This excitation results in an increase in the temperature of the water. The heat released by this increase in the temperature of the water is transmitted to the surface of the structure to be inspected. This heat has the consequence of heating and deforming a region of the surface of the structure.

The system of the disclosed embodiments also comprises an image-taking device 5 situated outside the structure 1 to be inspected and taking at least one image of the surface of the structure. In one embodiment, the image-taking device is a thermal camera or an infrared camera that takes an image of the structure to be inspected. The thermal camera and the infrared camera have the particular feature of analyzing the different image-taking elements as a function of their thermal radiation. Each of them can be used to identify the hot points in an image. In the invention, such a camera is used to identify the hot regions of the structure 1 to be inspected. Each hot region corresponds to the position of an infiltration of water into the internal layer of the structure In another embodiment, the image-taking device is a holographic interferometry device that takes two holographic images of the surface of the structure 1 to be inspected. These holographic images are superimposed, thus enabling the detection of the deformed regions. In the invention, this holographic interferometry device detects the regions of the surface of the structure 1 that have got deformed under the effect of heat. These deformed regions each correspond to the location of an infiltration of water into the internal layer of the structure.

Whatever the type of image-taking device (holographic interferometry device or camera), the images obtained of the surface of the structure to inspected show the noteworthy regions of said surface, i.e. the hot regions or the deformed regions which correspond to a point of water within the structure.

In one example of the system of the disclosed embodiments, the generator 2 sends out microwaves at a frequency of 2.45 GHz. The microwaves do not cross the carbon skins of the sandwich structure. They remain contained in the enclosed structure. They can therefore be emitted without risk for the security of the maintenance staff.

In one embodiment, the emitter is an irremovable antenna. It is therefore installed permanently in the structure. In this case, each part of the aircraft liable to be inspected comprises at least one fixed antenna. Such an antenna may comprise:

a base fixed to the carbon skin of the structure to be inspected. The base has an input terminal capable of receiving the waveguide 6.

a conductive rod fixed to the base and forming a protruding feature in the internal layer of the structure to be inspected. This conductive rod transmits microwaves into the structure 1. The length of this conductive is rod is adapted to the structure to be inspected. For example, the conductive rod may have a length of about 30 mm.

In another embodiment, the emitter is a removable antenna. In this case, a hole is preformed in the carbon skin of the structure to be inspected. In the inspection phase, the antenna is installed in this hole. Outside the maintenance phase, the hole is shut by means of a tight-sealing plug. This plug may, for example, be screwed into the structure. Thus, during the inspection of the structure, the plug is unscrewed and the emitter is fitted into the hole in place of the plug. When the inspection is over, the plug is screwed back into the hole. An emitter of this kind has the advantage of causing no drag in flight, especially when the structure is placed in the aerodynamic stream.

In another embodiment, the hole is filled with resin as soon as the structure is out of maintenance.

Whether it is fixed or removable, the emitter may be a radial antenna, i.e. an antenna sending in all directions of a plane, especially when the microwave emission power is high, or it may be a directional beam antenna, especially when the available power is lower.

Figure 2:
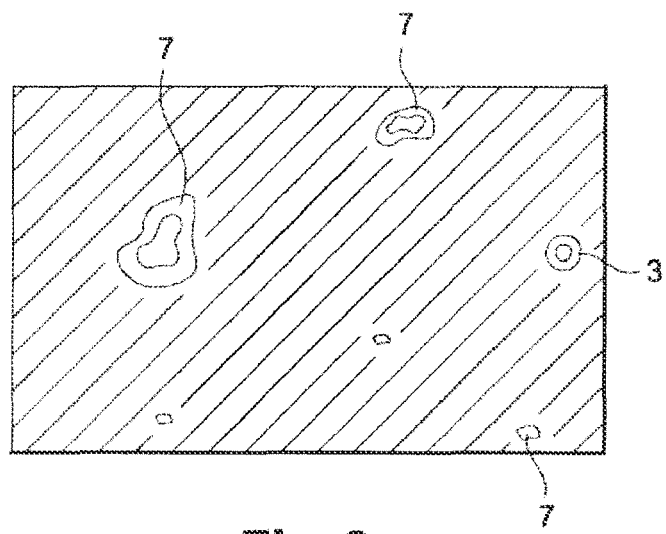
FIG. 2 is an example of an image obtained with an infrared camera according to the disclosed embodiments.

FIG. 2 shows an example of an image of the surface of a sandwich structure infiltrated with water. This image has been obtained with an infrared camera. In this image, a plurality of spots can be seen. Each spot corresponds to the detection of a hot region on the surface of the structure. One of these spots has a particularly round shape: it corresponds to the antenna 3. Since the location of the antenna is known, it is easy, in the picture, to identify the spots corresponding to the antenna relative to other spots. The other spots 7 detected correspond to hot points of the surface of the structure. Each hot point corresponds to the presence of water infiltrated into the structure. Thus, the image given by the infrared camera enables the identifying, on the external skin of the sandwich structure, of the hot regions whose location corresponds to the presence of water in the internal layer. Since only water is sensitive to the microwaves, all the hot regions detected on the surface of the sandwich structure correspond to a water-infiltrated region. Defects of construction are not detected.

Figure 3:
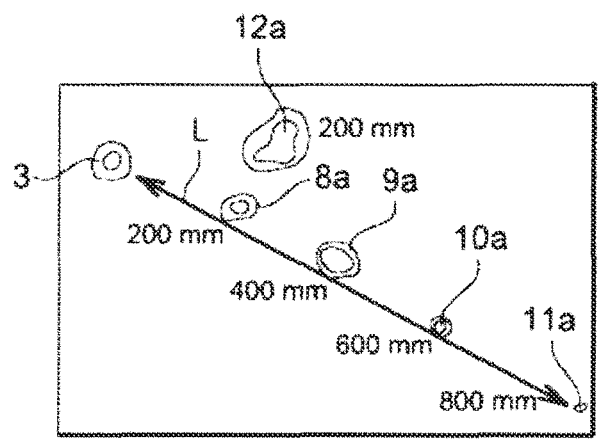
FIG. 3 is another example of an image obtained with the system of the invention, when the thermal signature is not homogeneous.

In the embodiments described here above, only one emitter is used to transmit microwaves in the internal layer of the surface to be inspected. The use of only one emitter may lead to a non-homogenization of the electromagnetic field in the structure. In this case, the water-infiltrated regions do not show any identical rise in temperature. The spots in the image have different aspects. An example of an image obtained with an infrared camera in which the thermal signature is not homogeneous is shown in FIG. 3. In this example, the emitter enables a detection of water in an 800 mm region. In this region, four hot points 8a, 9a, 10a, 11a, 12a are detected along the line L, in addition to the antenna 3: the hot point 9a is 400 mm bigger than the others; the hot point 11a is 800 mm smaller than the others.

Figure 4:
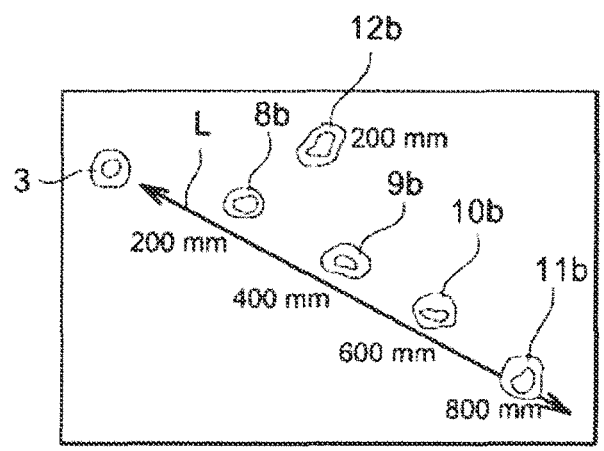
FIG. 4 is yet another example of an image obtained with the system of the invention, when the thermal signature is homogeneous.

To obtain homogeneous thermal signatures, corresponding to substantially identical tasks in the image, the invention proposes an embodiment in which two emitters are installed in the structure to be inspected. This has the effect of making the electromagnetic field in the structure homogeneous. The frequency of the second emitter may be different from that of the first emitter. The water-infiltrated regions then have a similar rise in temperature. The hot points in the picture therefore have a similar size, as can been seen in the example in FIG. 4. The detection of hot points 8b, 9b, 10b, 11b, 12b on the image is thus facilitated.

The examples of FIGS. 3 and 5 correspond to pictures obtained by means of an infrared camera. It is clear that a detection of the water-infiltrated regions with a homogeneous thermal signature can also be obtained with a holographic interferometry device, as described here above.

The system of the disclosed embodiments that has just been described has the advantage of enabling rapid heating time for the infiltrated water. This heating time is about 10 seconds to 1 minute. The rise in temperature of the surface of the structure to be inspected is therefore also faster than in the prior art. This enables fast inspection of the parts, without any disassembly. The total time taken to implement an acquired result is thus is less than half an hour. This reduction in the detection time therefore means that inspections can be made more frequently and therefore makes repairs less since they are done early, before the structure has undergone excessive deterioration.

Furthermore, this system has the advantage of being relatively compact since all it needs to heat the water is a compact microwave generator and one or more emitters situated inside the structure to be inspected.

The invention claimed is:

1. System for the detection and locating of water in a sandwich structure for aircraft, comprising a means to heat the water present in the intermediate layer of the sandwich structure and means to take at least one image of a surface of the sandwich structure, said image showing noteworthy regions of said surface corresponding to the presence of water in the intermediate layer,
   wherein the means used to heat the water comprise a device for emitting microwaves inside the sandwich structure at a frequency essentially equal to the resonance frequency of the water molecules, the device for emitting microwaves comprising:
   a microwave generator external to the sandwich structure,
   at least one microwave emitter situated inside the structure, and
   at least one waveguide to transmit the microwaves from the generator to the emitter.

2. System according to claim 1, wherein the means for taking images is an infrared camera or a thermal camera configured to detect a hot region on the surface of the structure, this hot region corresponding to the presence of water heated by the microwaves.

3. System according to claim 1, wherein the means for taking images is a holographic interferometry device configured to detect the deformed regions on the surface of the sandwich structure, these deformed regions corresponding to the presence of water heated by the microwaves.

4. System according to claim 1, wherein the microwave emitting device comprises two microwave emitters.

5. System according to claim 4, wherein the two microwave emitters emit at different frequencies.

6. System according to claim 1, wherein a microwave emitter is an irremovable antenna comprising a base fixed to the structure and a conductive rod situated within the structure.

7. System according to claim 1, wherein a microwave emitter is a removable antenna comprising a conductive rod installed in a hole of the structure, this hole being shut by a tight-sealing plug during flight.

8. Aircraft comprising a system for the detection and locating of water according to claim 1.

9. Method for the detection and locating of water in a sandwich structure for aircraft, comprising:
   emitting microwaves within the sandwich structure at a frequency essentially equal to the resonance frequency of the water molecules,
   taking at least one image of a surface of the sandwich structure, and
   detecting a noteworthy region on the image of the surface of said structure, this region corresponding to the presence of water in an intermediate layer of said sandwich structure.

* * * * *